United States Patent [19]

Barrett et al.

[11] Patent Number: 4,650,329

[45] Date of Patent: Mar. 17, 1987

[54] OPTICAL 3-D SIGNATURE DEVICE FOR DETECTING CHEMICAL AGENTS

[75] Inventors: Terence W. Barrett, Bethesda; John F. Giuliani, Kensington, both of Md.

[73] Assignee: The United States of America as represented by the Secretary of the Navy, Washington, D.C.

[21] Appl. No.: 676,044

[22] Filed: Nov. 29, 1984

[51] Int. Cl.⁴ .............................................. G01B 9/02
[52] U.S. Cl. .................................... 356/345; 356/361
[58] Field of Search ....................... 356/133, 345, 361; 250/227

[56] References Cited

U.S. PATENT DOCUMENTS

| | | | |
|---|---|---|---|
| 3,761,724 | 9/1973 | Dennis | 250/565 |
| 3,998,591 | 12/1976 | Eckfeldt | 356/445 X |
| 4,283,142 | 8/1981 | De Steur et al. | 356/319 |
| 4,321,057 | 3/1982 | Buckles | 356/445 X |

FOREIGN PATENT DOCUMENTS

| | | | |
|---|---|---|---|
| 913182 | 3/1982 | U.S.S.R. | 356/361 |
| 809952 | 12/1982 | U.S.S.R. | 356/345 |

OTHER PUBLICATIONS

Fork et al. "Dispersion in the Vicinity of an Optical Resonance" Applied Optics, vol. 3 #1, Jan. 1964, pp. 137-142.

Shang "Chromatic Dispersion Measurement by White-Light Interferometry on Metre-Length Single-Mode Optical Fibres" Electronics Letters (Aug. 20, 1981) vol. 17 #17, pp. 603-605.

Milburn et al. "Production of Squeezed States in a Degenerate Parametric Amplifier", Optics Communications, vol. 39, No. 6, Nov. 15, 1981, pp. 401-404.

Walls "Evidence for the Quantum Nature of Light", Nature, vol. 280, Aug. 9, 1979, pp. 451-454.

Brown et al. "Correlation Between Photons in Two Coherent Beams of Light" Nature, vol. 177, No. 4497, Jan. 7, 1956, pp. 27-29.

Brown et al. "I. Basic Theory: The Correlation Between Photons in Coherent Beams of Radiation", Proceedings of Royal Society, vol. 242, pp. 300-324.

Brown et al. "Interferometry of the Intensity Fluctuations in Light, II. an Experimental Test of the Theory for Partially Coherent Light", Proceedings of Royal Society, vol. 243, Jan. 14, 1958, pp. 291-319.

DeLange "Optical Heterodyne Detection", IEEE Spectrum, Oct. 1968, pp. 77-85.

Primary Examiner—Vincent P. McGraw
Attorney, Agent, or Firm—Sol Sheinbein; William T. Ellis

[57] ABSTRACT

An optical device for obtaining a 3-dimensional signature or a plurality of 2-dimensional signatures for a given sample in order to detect predetermined chemical agents. The device comprises a light channel with a first sensing optical fiber with a coating thereon which changes its absorptive and refractive properties in the presence of a predetermined chemical agent, and a second light channel with a reference optical fiber isolated from the sample. A scanning monochromator is utilized to apply light beams to the sensing and reference fibers, and an optical detector is used to cross-correlate the outputs from the sensing and reference fibers. A variable optical delay line is disposed in one of the fiber channels in order to scan from 0° to 360° in phase shift for each light frequency. A 2-dimensional cross-correlation is obtained for this scan at this frequency. The scanning monochromator is set to run through a series of light frequencies in a given bandwidth. A 2-dimensional cross-correlation phase scan is obtained at each different light frequency. A 3-dimensional cross-correlation may then be obtained (cross-correlation value vs frequency vs phase delay) to provide a signature for a given sample which can be compared to known samples. The device may utilize separate channel bandwidth filters to obtain squeezed states and high S/N ratios.

30 Claims, 3 Drawing Figures

OPTICAL 3-D SIGNATURE DEVICE FOR DETECTING CHEMICAL AGENTS

BACKGROUND OF THE INVENTION

The present invention relates generally to an optical detection device for chemical agents, and more particularly to a unique device and method for achieving 2 and 3-dimensional discrimination of chemical agents with high signal-to-noise detection.

Current chemical agent waveguide detection devices are designed to monitor the absorption changes of light when the waveguide is immersed in a sample with a chemical agent. Such waveguide detection devices are relatively insensitive because they rely only on absorption changes of light in order to discriminate between chemical agents and because the amplification is by electronic means, which are subject to noise interference.

OBJECTS OF THE INVENTION

Accordingly, it is an object of the present invention to discriminate between chemical agents by detecting and monitoring changes in absorption and changes in phase due to refractive index changes.

It is a further object of the present invention to significantly increase the sensitivity of optical agent detecting devices.

It is yet a still further object of the present invention to discriminate between chemical agents by means of 2-dimensional and 3-dimensional signatures of those chemical agents.

It is a still further object of the present invention to discriminate between chemical agents by means of a 2-photon coherent state correlation function having a very high signal-to-noise ratio with squeezed states.

It is yet a further object of present invention to eliminate electronic interference problems in the discrimination between chemical agents.

Other objects, advantages, and novel features of the present invention will become apparent from the detailed description of the invention, which follows the summary.

SUMMARY OF THE INVENTION

Briefly, the above and other objects of the present invention are achieved in an optical detection device for chemical agents comprising a first optical waveguide with a first coating disposed therearound, with the coating having the characteristic of changing its optical properties in the presence of predetermined chemical agents, thereby affecting at least one parameter of light propagating through the first optical waveguide, the first optical waveguide being disposed in a location to detect predetermined chemical agents. The device further comprises a reference optical waveguide, means for isolating the reference optical waveguide from exposure to chemical agents, means for directing a light beam at a particular frequency into the first and reference optical waveguides to propagate therethrough to provide a first and a reference light outputs, respectively, and means for changing the particular frequency of the light beam being directed into the first and reference optical waveguides in a sequential manner across a desired band of frequencies. Additionally, a first variable optical delay line is disposed in one of the first or reference optical waveguides for delaying the light propagating therein by a predetermined delay, along with means for varying this predetermined delay through a predetermined degree range of phase shift for each particular frequency directed into the first and reference optical waveguides. Means for detecting the cross-correlation of the first and reference light outputs is included to obtain a precise signature for the chemical agents in a sample.

In a preferred embodiment, the optical waveguides comprise optical fibers, and the detecting means comprises an optical detector and means for recording the output signal from the optical detector in conjunction with the particular frequency generated for that output by the frequency changing means and the time delay generated by the first variable optical delay line for that output.

In order to obtain squeezed states to thereby enhance the signal-to-noise ratio, a laser is used for generating a coherent light beam, and means are provided for applying the coherent light beam with a narrow bandwidth $\Delta f_1$ to the first optical waveguide, and for applying the coherent lightbeam with a wide bandwidth $\Delta f_2$ to the reference optical waveguide, wherein $\Delta f_1 \cdot \Delta f_2$ is greater than or equal to $\frac{1}{4}$.

DETAILED DESCRIPTION OF THE PREFERRED EMBODIMENT

Figure 1:
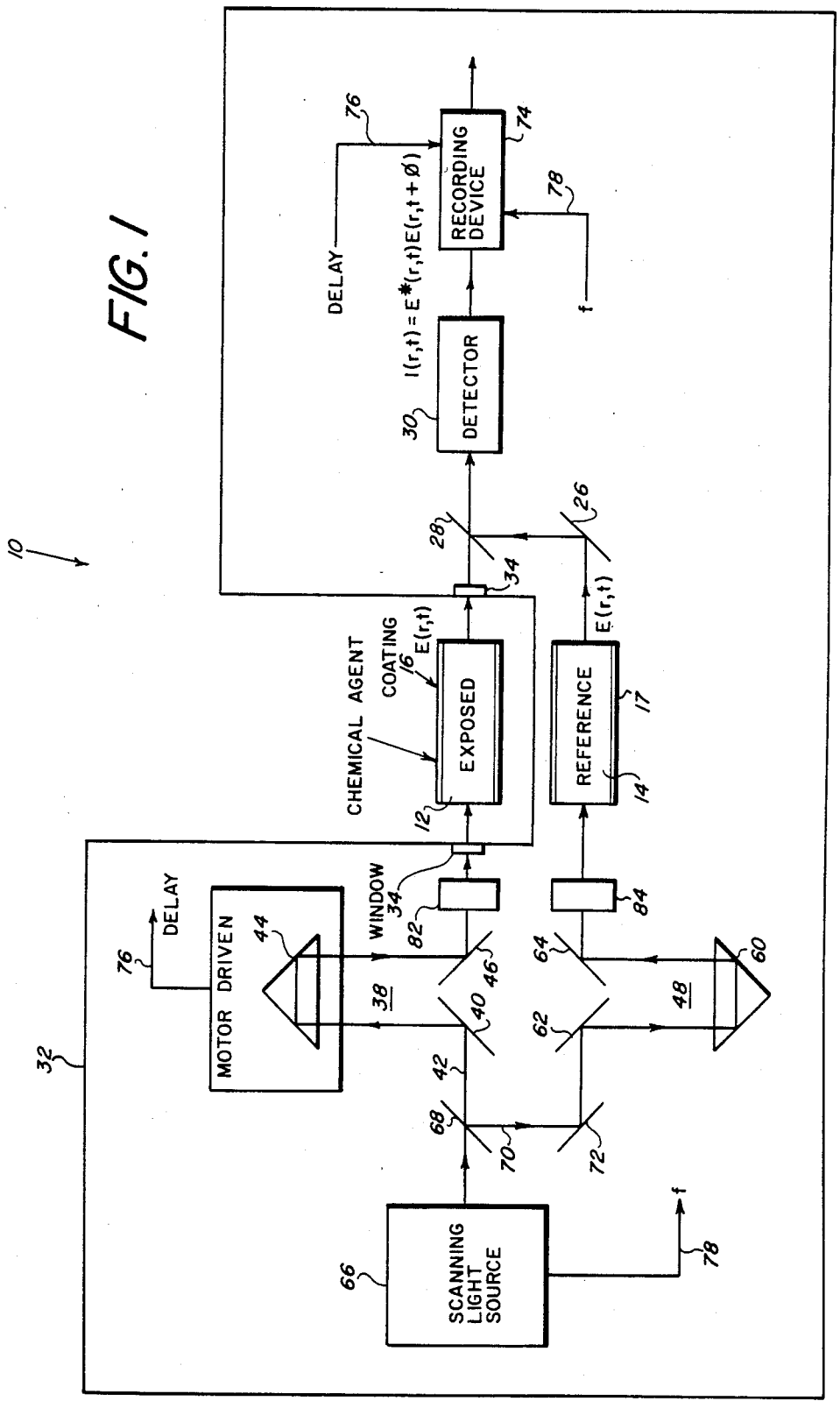
FIG. 1 is a schematic block diagram of one embodiment of the present invention.

Referring now to FIG. 1, there is shown a chemical detection device 10 of the present invention. The device 10 comprises a first optical channel 11 including an optical waveguide 12 and a second optical channel 13 including a reference waveguide 14. The first optical waveguide 12 has a first coating 16 disposed therearound, with the coating having the characteristic of changing its optical properties in the presence of predetermined chemical agents, thereby affecting at least one parameter of light propagating through the first optical waveguide. Typically, the coating 16 is chosen such that it will change its refractive index and its absorption spectrum in the presence of the predetermined chemical agents which are absorbed into the coating. The change in refractive index causes a change in the phase of the light propagating in the optical waveguide, and also causes a change in transmission losses of light out of the waveguide. These changes are detected by means of a cross-correlation or Heterodyne beating of the outputs from the channels 11 and 13 at an optical detector 30. The basic equation for the cross-correlation at the detector 30 is $I(r,t) = E_1(r,t) E_2(r, t + \phi)$, where $E_1(r,t)$ is the output from the reference channel 13, $E_2(r, t + \phi)$ is the output from the signal carrying first channel 11, and $\phi$ is the phase shift caused by the change in the index of refraction.

Figure 2:
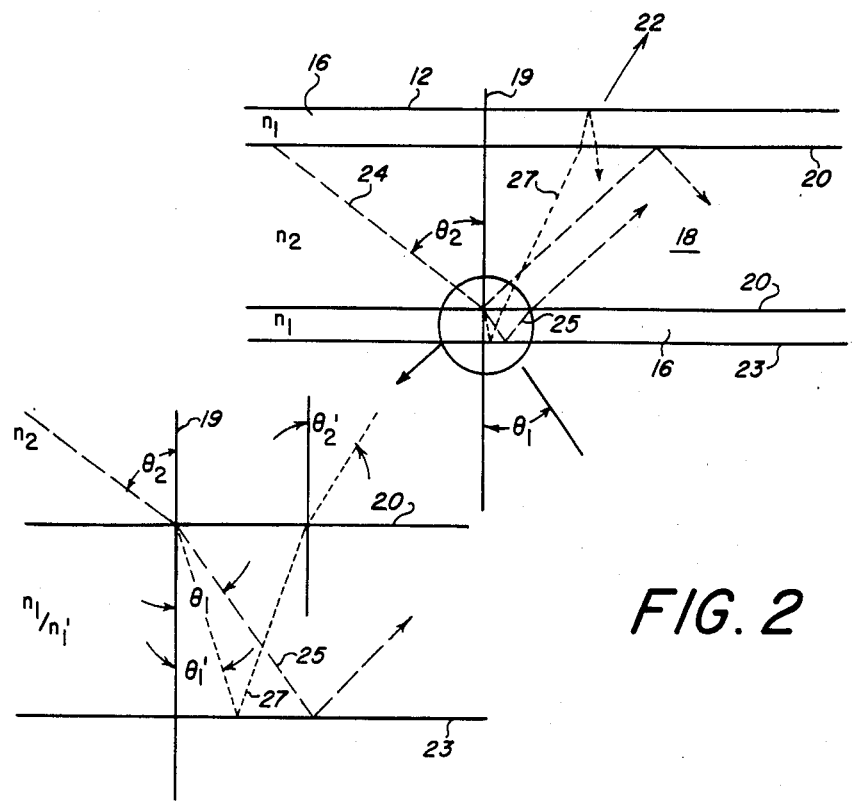
FIG. 2 is a schematic diagram of the light propagation in a coated fiber.

The above described transmission loss and phase change effects can be better understood by reference to FIG. 2, which shows a brief section of the optical waveguide 12 with the coating 16. The optical waveguide is designed with an internal transmission section 18 with a refractive index of $n_2$ and a surrounding covering or coating 16 with a refractive index $n_1$, where $n_1$ is greater than $n_2$. It is known that light, in propagating along the length of this waveguide 12, is internally reflected back and forth between the waveguide walls. Efficient propagation along the length of the waveguide 12 takes place provided the light does not impinge on the interface 20 with an angle greater than the well known critical angle for light propagation. If the angle of light impingement is greater than the critical angle, then there is no longer complete internal reflection within the waveguide 12 and some light 22 is lost via transmission out of the waveguide. A light beam 24, illustrated with dashed lines, is shown in FIG. 2 being internally reflected within the waveguide 12. It can be seen that a component 25 of this light beam is refracted by the coating 16 in accordance with Snell's law: $n_2/n_1 = \sin \theta_2 / \sin \theta_1$, where $\theta_1$ and $\theta_2$ are angles which the beam 24 makes with a line 19 normal to the interface 20. This refracted light beam component 25 is shown in more detail in the blowup of FIG. 2. The component 25 reflects off of the interface 23 between the coating 16 and the external environment.

The reference waveguide 14 is designed to propagate light in much the same manner as the first optical waveguide 12. The outputs from the first optical waveguide 12 and the reference waveguide 14 are combined by some form of combining device such as, by way of example, appropriately positioned mirrors 26 and 28, so that both of the outputs impinge on a detector 30. Typically, in order to ensure that the reference waveguide 14 propagates light in the same manner as the first waveguide 12 when the first waveguide 12 is not exposed to a chemical agent, the reference waveguide 14 is coated with a coating 17. Preferably, this coating 17 is the same as the coating 16. Thus, refraction of the light beam component 25 may also represent the light beam refraction in the coating 17 in the reference waveguide 14. Accordingly, if coherent n-phase light beams are propagated in the first waveguide 12 and the reference waveguide 14, and assuming that the two waveguides have been zeroed to compensate for any differences in length, then there should be an exact correlation detected by the detector 30.

When the first waveguide 12 is exposed to a sample with predetermined chemical agents therein to which the coating 16 is sensitive, then the coating 16 changes its refractive index to $n_1'$. This change in the refractive index of the coating 16 causes a change in the angle of refraction $\theta_1$ of light in the waveguide 12 to a new angle of refraction $\theta_1'$ in accordance with Snell's Law: $n_1'/n_2 = \sin \theta_1' / \sin \theta_2'$. This change in the angle of refraction caused by the change in the index of refraction for the coating 16 is either an increase or a decrease in comparison to the no-sample situation. In FIG. 2, the new refraction angle is illustrated by the dotted line light ray 27, which represents an angle for a decreased index of refraction $n_1'$. This change can be seen in comparison to the ray 25 which can be viewed as the ray propagating in the reference waveguide 14 which is isolated from the chemical sample. Since $n_1$ decreased to $n_1'$, then $\theta_1$ decreased to $\theta_1'$. Although $n_2$ remained the same, when the light beam reflected off of the interface 23 and propagated through the interface 20, the angle $\theta_2$ decreased to $\theta_2'$ in accordance with Snell's law.

Whether the index of refraction of the coating 16 increases or decreases over the no-sample situation, the change will cause a change in the angle of internal reflection which, in turn, causes a change in phase of the light propagating in the waveguide 12. In the example of FIG. 2 with a decreased index of refraction for the coating 16, the light ray 25 in waveguide 12 is propagating slower than the light ray 24 in the reference waveguide 14 because of the decreased angle of refraction of the light.

An additional effect is obtained if the angle of internal reflection increases beyond the well known critical angle, such that a certain portion of the light is actually transmitted through the coating 16 and completely out of the fiber. This transmitted light loss is designated by the arrow 22.

In contradistinction to the above, the reference waveguide 14 is purposely isolated from the sample with its chemical agents, to thereby ensure an essentially constant light propagation through the reference waveguide 14. Accordingly, when light is propagated in the waveguides 12 and 14, and the waveguide 12 is exposed to a sample with predetermined chemical agents which change the index of refraction of its coating 16, then a distinct phase difference is be obtained between the light propagating in the waveguide 12 relative to the light propagating in the reference 14. This distinct phase change causes a change in the correlation output from the optical detector 30. Likewise, if there is light transmission loss from the optical waveguide 12 due to the angle of internal reflection in the waveguide 12 exceeding the critical angle, then there is also a detected amplitude change in the detector 30. Also, if the absorption spectrum of the coating 16 is changed by the chemical agents, then more or less light is absorbed by the coating 16 to provide an additional change in the amplitude.

The actual isolation of the reference waveguide 14 is accomplished in FIG. 1 by means of an isolation housing 32. The housing 32 includes opposing windows 34 therein in order to propagate light from a light source into one end of the first optical waveguide 12 and out the other end thereof to impinge on the detector 30.

Figure 3:
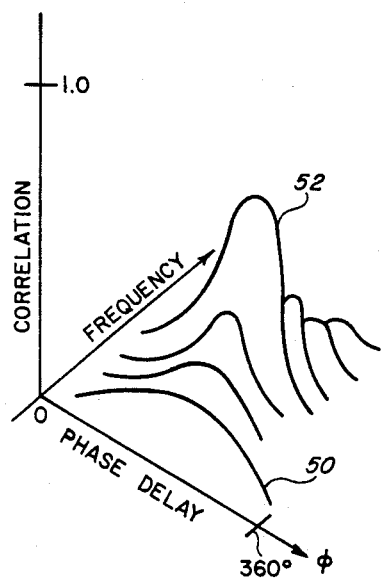
FIG. 3 is a perspective drawing of a 3-dimensional chemical agent signature.

In order to obtain a two-dimensional cross-correlation of the light beam, a variable delay circuit may be disposed in one of either the reference channel or the first optical channel. This variable delay may be used to insert an optical delay scanned over a certain phase shift range into one of the channels. Preferably, this optical delay scan range should be over the range 0° to 360°. Note that filter channel may be delayed since the phase shift obtained is a relative measure. FIG. 3 illustrates a curve 50 for such a two-dimensional cross-correlation obtained from the detector 30. From such a two-dimensional curve 50, the phase delay for the highest point in the correlation output can be determined.

As noted above, this variable phase delay may be located in either the first channel 11 or the reference channel 13. For purposes of illustration, FIG. 1 illustrates a variable delay line 38 in the first optical channel 11. This variable delay line 38 may be implemented in a variety of delay configurations. In the example of FIG. 1, the variable delay line 38 is shown as including a reflecting mirror 40 for reflecting a light beam 42 up to a corner mirror 44 which is mirrored on two sides of a right angle corner. The corner mirror 44 operates to reflect the light through an angle of 180° to a mirror 46. The mirror 46 then reflects the light into the first optical waveguide 12. In order to make this delay variable, the corner mirror 44 may be connected to a motor drive shaft in order to scan the corner mirror 44 through a length change relative to the mirrors 40 and 46 which is equivalent to a phase shift of 0° to 360°. Note that this phase scanning may also be accomplished manually.

A second variable delay line 48 may be disposed in the other of the two optical channels 11 and 13 in order to permit the zeroing of the two optical beam outputs at the detector 30 when no sample is present. It should be noted that this variable delay line 48 may be used to place the two optical output beams from the waveguides 12 and 14 exactly in phase or ninety degrees out of phase, or at some other phase shift difference. The adjustment of the delay line 48 so that the optical beams cancel at the detector 30 (90° phase shift) when no sample is present yields the most sensitive readings for the device. The variable delay line 48 may be implemented simply by a corner mirror 60 in conjunction with reflecting mirrors 62 and 64 in the same manner as the variable delay line 38.

It is also known that the refractive index is frequency dependent due to the Kronig-Kramers relation between the refractive index and the absorption of light. Accordingly, the variation of the phase shift over a range of 0°-360° may not yield the highest correlation value at a given frequency. Thus, not only should the phase shift be scanned over a predetermined range, but also the frequency of the optical beam should be scanned over a desired frequency range. In order to implement this frequency scanning, a scanning light source 66 is provided. This scanning light source may be implemented in a number of configurations to provide either coherent or incoherent light. By way of example, a Mercury arc lamp may be utilized in conjunction with a scanning monochromator. The Mercury arc lamp provides light frequencies at all of the visible frequencies. The monochromator operates to pick out each desired frequency sequentially and provide it as an output. By way of example, the Mercury arc lamp could be a Bausch & Lomb (Rochester, N.Y.) mercury arc lamp set to provide a visible wavelength range of 450 nm-620 nm. The scanning monochromator could then be set to pick out each frequency sequentially over the wavelength range 450 nm to 620 nm and provide it as an input to the optical waveguides 12 and 14. The scanning monochromator could be set to dwell at each integer frequency for a sufficient period of time to permit the variable phase delay 38 to scan over the delay range 0°-360° in phase shift for that frequency. It should be noted that the larger the dwell time at each frequency, the more accurate is the data yielded from that scan. A scanning monochromator capable of performing the above described scan of frequencies over the full visable spectral range is the Raman spectrometer built by Spex Industries, Metuchen, N.J., under the trade name RAMA-LOG. It should be noted that Mercury Arc lamps normally are sold with a monochromater attached. Thus, the present scanning could also be implemented simply by gearing the monochromator dials to a motor drive shaft for automatic scanning.

From the above, it can be seen that the present design can be implemented with an incoherent light input. In this regard, the operation of the monochromator to select out a given frequency from the Mercury Arc lamp source is sufficient to permit the detection of optical phase changes between the two channels. However, the light source 66 can also be implemented by means of a scanning laser system for generating coherent light. Such a laser system capable of scanning across the entire visable range (via the serial introduction of the appropriate laser dyes) is manufactured by Coherent, Inc. of Palo Alto, Calif.

It should be noted that the above described wavelength range is set forth by way of example only. Any other desirable wavelength range can be utilized for the scanning. It should also be noted that the frequency selected for each dwell time need not be an integer frequency. In order to provide a light beam to both channel waveguides, the light beam from the scanning light source 66 may simply be divided into two light beams for application to the first optical waveguide 12 and the reference waveguide 14. Again, this light beam dividing function may be implemented in a number of configurations. In FIG. 1, the light dividing function is implemented by a beam splitting mirror 68 set at the appropriate angle, for dividing the beam into a beam on line 42 and a beam on line 70. The light beam on line 42 is reflected via the mirror 40 to the corner mirror 44 of the optical delay line 38. The light beam on line 70 is reflected via the mirror 72 to the mirror 62 for the delay line 48.

Referring again to FIG. 3, it can be seen that a plurality of two-dimensional correlation versus phase delay scan curves are set forth. Each individual curve is for a different frequency setting of the light beam. The curve 52 represents the frequency where the maximum correlation was obtained for that particular sample. Accordingly, it can be seen that this plurality of two-dimensional correlation versus phase delay curves, when displayed together, provide a three-dimensional signature for the chemical agents in the sample. Thus, there is a unique signature comprising a correlation versus phase versus frequency three-dimensional figure for each chemical agent to which the coating 16 is sensitive. Accordingly, this three-dimensional figure can be utilized to very finely discriminate between similar chemical agents. In essence, this three-dimensional figure provides a very accurate measure of the changes in the refractive index and the changes in the absorption spectrum in the outer coating 16 resulting from the presence of certain chemical agents.

In order to provide the above described two-dimensional and three-dimensional signatures, it is desired that some form of storage device be utilized to store the cross-correlation outputs from the detector 30. In FIG. 1, a recording device 74 is utilized for recording the cross-correlation outputs from the detector 30. This recording device should include an input on line 76 which is proportional to the position of the motor drive shaft for translating the corner mirror 44 in the motor driven variable delay line 38 in order to provide the phase delay to which the motor driven delay line 38 is set for a given cross-correlation value. Likewise, the frequency for a given variable phase delay scan should be provided via the lines 78 from the scanning light source 66. The recording device 74 could then list the cross-correlation value with a given frequency and a given delay. It can be seen that if only one or two frequencies are to be utilized, then only one or two two-dimensional curves need to be plotted of the correlation value versus the phase delay scan. However, if a plurality of frequencies are to be scanned across a given bandwidth, then it may be desirable to plot out a three-dimensional figure on paper or on a CRT screen.

The recording device 74 may be implemented in a variety of configurations. In one embodiment, a Raman spectrometer may be utilized in conjunction with an analog/digital converter in order to record the cross-correlation values versus frequency and versus phase delay. For example, the RAMALOG Raman spectrometer made by SPEX, Inc., noted previously, may be utilized to generate the 3-D signature plots via the use of the DM1B controller in the device. This Raman spectrometer could then be connected to a CRT screen. It should be noted that Tektronix also manufactures a 3-D computing device which could be utilized in the present instance.

The present chemical agent detecting device is capable of detecting a wide variety of chemical agents including nerve agents, ammonia, cyanide, etc. The type of chemical agents that can be detected will depend on the coating 16 disposed over the optical waveguide 12. For example, oxazine dye may be utilized as the coating 16 in order to detect chemical warfare simulated nerve gases such as GBGD dimethyl methyl phosphonate, propionic acid, or triethyl phosphate. The oxazine dye produces a color reaction/index of refraction change when exposed to any of the above cited nerve gas simulates. Another coating that could be utilized is lead phthalocyanine for detecting the nerve agent simulate DMMP. Different metals such as cobalt, or copper could be utilized in place of the lead in the phthalocyanine molecule of in this coating. Another coating that could be utilized is lead porphyrin for detecting nerve agent simulant DMMP or polyethylene maleate, which strongly reacts with DMMP vapor. There are also a variety of polymer coatings which act to change their index of refraction in the presence of DMMP. By way of example, such a polymer coating is polyvinyl pyrrolidone.

It should be noted that the thickness of the coating 16 is not critical so long as the coating is thick enough so that enough dye or polymer, etc. is in the coating to obtain a measurable change in the index of refraction in the presence of predetermined chemical agents. Typically, this thickness may be on the order of 1 micron.

It is noted that some coatings such as the polymer coatings adsorb the chemical agent but can reversibly desorb the agent. This reversibility means that the polymer coating does not have a chemical reaction with the chemical agent so that when the sample vapor with the chemical agent is removed, then the polymer coating returns to its original condition. However, some coatings are nonreversible in nature. These coatings, such as the dye coatings, are cumulative and act essentially like dosimeters. The chemical agents in the sample vapor modify the structure of these dye coatings permanently. However, these dye coatings can continue to be used simply by comparing them to a similarly affected reference waveguide.

It is noted that two-photon correlation is obtained at the detector 30. Thus, if a laser source is utilized in the scanning light source 66 in order to obtain coherent beams of light in the waveguides 12 and 14, then it is possible to obtain two-photon coherent state correlation with very high signal-to-noise ratios and the possibility of squeezed states. For a discussion of two-photon coherent states and squeezed states, see the article "Production of Squeezed States in a Degenerate Parametric Amplifier" by G. Milburn and D. F. Walls, Optics Communications, Vol. 39, No. 6, page 401 (Nov. 15, 1981). See also G. J. Milburn and D. F. Walls, Physical Review A27, 1983, 392; and P. A. Lakshmi and G. S. Agarwal, Physical Review A29, 1984, 2260. In essence, squeezed states are generated when the uncertainties in two components of a complex radiation field amplitude are unequal though their product yields a minimum uncertainty state. Such fields have less fluctuations in one quadrature than a coherent state, at the expense of increased fluctuations in the other quadrature. Such squeezed states can be implemented simply by providing an input coherent light beam into the optical waveguide 12 with a narrow bandwidth $\Delta f_1$, while providing a light input into the reference waveguide 14 with a wide bandwidth $\Delta f_2$. Since this squeezed state configuration is based on the quantum mechanical uncertainty principle, the coherent laser light beam bandwidths must satisfy this uncertainty relationship in accordance with the following equation $$\Delta f_1 \cdot \Delta f_2 \geq \tfrac{1}{4}.$$

This squeezed state configuration may be implemented simply by providing a laser light source in the scanning light source 66 with a wide bandwidth, and then inserting a light frequency filter 82 with a narrow bandwidth $\Delta f_1$ in the first channel 12, while inserting a wide bandwidth light filter 84 in the reference channel 14. The signal-to-noise ratio realized from such a squeezed state configuration is significantly lower than other designs. In particularly, the signal-to-noise ratio will be $f_1/\Delta f_1$. The small changes in $f_1$ provide the information for the signature for the chemical agents. The cross-correlation signal-to-noise ratio is $f_2/\Delta f_2$. Since $\Delta f_2$ is relatively large, the signal-to-noise ratio for the cross-correlation is relatively low, meaning that most of the noise is concentrated in this larger bandwidth reference channel.

It should be noted that the first and the reference waveguides 12 and 14 can be implemented simply by optical fibers. Preferably, these optical fibers do not have their own cladding, but utilize the coatings 16 and 17, respectively, as their claddings. Typically, the optical fibers simply may be glass with an index of refraction of on the order of 1.49. The coatings may then have an index of refraction of on the order of 1.6–1.9. It should be noted however, that it is possible to use an optical fiber with a cladding in addition to the coatings 16 and 17.

Typically, the present design set forth in FIG. 1 will be used to test a sample of vapor for predetermined chemical agents. However, it should be noted that the device of FIG. 1 could also be utilized to test for chemical agents in liquid by means of a liquid-filled jacket. In such a configuration, the liquid in the jacket would be sensitive to the predetermined chemical agents. The chemical agents could either be flowed through the liquid or could be bubbled through the liquid in the form of a gas. If predetermined chemical agents are present in this gas, then the liquid within the jacket changes its absorption spectra and thus its index of refraction.

It should be noted that in the preferred embodiment the reference waveguide 14 has a coating 17 identical to the coating 16 on waveguide 12. However, a different coating 17 could be utilized or a different form of reference device could be utilized and the reference and the first waveguide 12 could be zeroed electronically.

In operation, the present device for each particular frequency scans over a desired delay range, typically 0 degrees–360 degrees in phase shift. If none of the predetermined chemical agents to which coating 16 is sensitive are present in a given sample, then cross-correlation values from +1 at zero degrees through −1 at 180 degrees are expected with little variation therein. However, if a predetermined chemical agent is present, then that chemical agent will be adsorbed in the coating 16 to thereby change its adsorption spectrum and its index of refraction. Since the index of refraction of the coating 16 is changed, there is a distinct phase shift which is detected by the detector. Likewise, because the absorption spectrum is changed, the light frequencies being absorbed, i.e., removed from the light beam propagating in the waveguide 12, are different. Thus, by sequentially scanning through the desired band of frequencies, this change in the absorption spectrum can be detected. For example, if the coating 16 normally absorbs 700 nm wavelengths with no chemical agent present, then it might be changed to have an absorption spectrum which absorbs 650 nm with a certain chemical agent present. Accordingly, when the frequency of the light is scanned to the 650 nm wavelength, then an appreciable intensity change in the light detected by the detector 30 is realized. Additionally, the intensity will also change if the refractive index is changed sufficiently so that the light beam is impinging on the interface 20 between the glass fiber 18 and the coating 16 with an angle greater than the critical angle so that a certain portion of the light beam is lost by means of transmission out through the fiber walls.

The optical detection device for chemical agents described in the present design incorporates a unique method and means for achieving high signal-to-noise detection. The design incorporates the use of discrimination between chemical agents by means of changes in absorption of the coating 16 when a given chemical agent is present, and changes in the phase due to refractive index changes in the coating 16. Two-dimensional cross-correlation functions are generated of the correlation value versus phase delay in order to provide chemical agent discrimination. Additionally, 3-dimensional cross-correlation functions can be obtained by also scanning the frequency of the light beam over a predetermined frequency bandwidth such that the cross-correlation value versus the phase delay versus the frequency provides a unique signature for a chemical agent. This procedure provides a sensitivity for detecting chemical agents of on the order of parts per billion. This procedure also utilizes heterodyne beating to enhance the signal-to-noise ratio and discrimination, rather than electronic methods. The present design has very high sensitivity due to its detection of both changes in the absorption spectrum of the coating and the phase change due to the change in refractive index in the presence of a chemical agent. Thus, two and three dimensional signatures for chemical agents can be determined.

The output signal for this optical detection device configuration is a two-photon coherent state correlation function having a very high signal-to-noise ratio and the possibility of squeezed states. The squeezed states can be implemented simply by utilizing a coherent light beam source in conjunction with bandwidth filters on each of the waveguide channels. The use of squeezed states permits even higher signal-to-noise levels.

The present design does not use electronic methods which are susceptible to electronic interference in correlating the waveguide outputs to obtain the cross-correlation. This design can be made compact and portable by using a small low power light source in conjunction with solid state photo-transistors and amplifiers.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. An optical detection device for chemical agents comprising:
    a first optical waveguide with a first coating disposed therearound, said coating have the characteristics of changing its optical properties in the presence of predetermined chemical agents, thereby affecting at least one parameter of light propagating through said first optical waveguide, said first optical waveguide being disposed in a location to detect predetermined chemical agents;
    a reference optical waveguide;
    means for isolating said reference optical waveguide from exposure to said chemical agents;
    means for directing a coherent light beam at a particular frequency into said first and reference optical waveguides to propagate therethrough to provide first and reference light outputs, respectively;
    a first variable optical delay line disposed in one of said first or reference optical waveguides for delaying the light propagating therein by a predetermined delay;
    means for varying said predetermined delay through a predetermined degree range of phase shift for said particular frequency directed into said first and reference optical waveguides; and
    means for detecting a cross-correlation of said first and reference light outputs to thereby obtain a precise signature characterized by increased signal-to-noise ratio of said light outputs due to a squeezed state relation of two photons emerging from the respective waveguides.

2. An optical chemical detection device as defined in claim 1, wherein said first coating is of the type that changes its refractive index in the presence of predetermined chemical agents.

3. An optical chemical detector as defined in claim 2, wherein said detecting means comprises:
    an optical detector; and
    means for recording the output signal from said optical detector in conjunction with the particular frequency f generated for that output by said frequency changing means and the time delay generated by said first variable optical delay line for that output.

4. An optical chemical detection device as defined in claim 3, wherein said frequency changing means includes a laser for generating a coherent beam of light.

5. An optical chemical detection device as defined in claim 4, further comprising means for applying said coherent light beam from said laser with a narrow bandwidth $\Delta f_1$ to said first optical waveguide, and applying said coherent light beam from said laser with a wide bandwidth $\Delta f_2$ to said reference optical waveguide, wherein $$\Delta f_1 \cdot \Delta f_2 \geq \frac{1}{4},$$

in order to obtain a very high signal-to-noise ratio.

6. An optical chemical detection device as defined in claim 5, wherein said narrow and wide bandwidth light beam applying means comprises:

a narrow bandwidth light filter with a bandwidth $\Delta f_1$ disposed across the input to said first optical waveguide; and a wide bandwidth light filter with a bandwidth $\Delta f_2$ disposed across the input to said reference waveguide.

7. An optical chemical detection device as defined in claim 6, wherein said first and said reference optical waveguides are optical fibers.

8. An optical chemical detection device as defined in claim 7, wherein said reference optical waveguide has a second coating disposed therearound for affecting the light propagating in said reference optical waveguide in approximately the same way as the light propagating in said first optical waveguide is affected by said first coating with no predetermined chemical agents present.

9. An optical chemical detection device as defined in claim 8, wherein said light beam frequency changing means comprises a scanning monochromator.

10. An optical chemical detection device as defined in claim 9, wherein said delay varying means comprises means for varying said predetermined delay through a range of 0° to 360°.

11. An optical chemical detection device as defined in claim 10, wherein said light beam directing means includes a second variable optical delay line for delaying the light applied to the other optical waveguide by a second delay.

12. An optical chemical detection device as defined in claim 11, wherein said first and second coatings disposed on said first and said reference optical waveguides, respectively, are liquid-filled jackets, with the liquids in said liquid-filled jackets being sensitive to predetermined chemical agents.

13. An optical chemical detection device as defined in claim 11, wherein said first coating is oxime dye.

14. An optical chemical detection device as defined in claim 11, wherein said first coating is lead phthalocyanine.

15. An optical chemical detection device as defined in claim 11, wherein said first coating is a polymer coating.

16. An optical chemical detection device as defined in claim 1, wherein said first coating is a polymer coating.

17. An optical chemical detector device as defined in claim 1, wherein said first coating is oxime dye.

18. An optical chemical detection device as defined in claim 1 further comprising means for applying said coherent light beam to said first optical waveguide with a narrow bandwidth $\Delta f$, and to said reference optical waveguide with a wide bandwidth $\Delta f_2$, wherein $$\Delta f_1 \cdot \Delta f_2 \geq \tfrac{1}{2},$$

in order to obtain a very high signal-to-noise ratio.

19. An optical chemical detection device as defined in claim 1 further comprising:
means for changing said particular frequency of said light beam being directed into said first and reference optical waveguides in a sequential manner across a desired band of frequencies; and
means for varying said predetermined delay through a predetermined degree range of phase shift for respective particular frequencies directed into said first and reference optical waveguides.

20. A method for optically detecting chemical agents by obtaining a precise chemical agent signature in a device including a first optical waveguide with a first coating therein which has the property of changing its refractive index and absorption spectrum in the presence of predetermined chemical agents, thereby affecting at least one parameter of light propagating through said first optical waveguide, said first optical waveguide being disposed in a location to detect predetermined chemical agents, and a reference optical waveguide isolated from exposure to chemical agents, comprising the steps of:

exposing said first coating of said first optical waveguide to a sample possibly containing predetermined chemical agents;

directing a coherent light beam at a particular frequency into said first and reference optical waveguides to propagate therethrough to provide a first and a reference light outputs, respectively;

delaying the light beam propagating in either said first or said reference optical waveguides by a predetermined delay, with said predetermined delay being varied through a predetermined degree range of phase shift for said particular frequency directed into said first and reference optical waveguides;

determining a cross-correlation of said first and reference light outputs over said predetermined degree range of delay variation; and repeating said directing, delaying and cross-correlation determining steps for each new particular frequency directed into said first and reference optical waveguides to thereby obtain a precise cross-correlation signature characterized by increased signal-to-noise ratio of said light outputs due to a squeezed state relation of two photons emerging from the respective waveguides.

21. A method as defined in claim 20, wherein said cross-correlation determining step includes the steps of:
optically detecting said first and reference light outputs; and
recording the optically detected light outputs in conjunction with the particular frequency of the light for that output and the variable predetermined delay.

22. A method as defined in claim 21, wherein said light beam directing step includes the step of generating and directing a coherent beam of light.

23. A method as defined in claim 22, wherein said light beam directing step includes the step of applying said coherent light beam with a narrow bandwidth $\Delta f_1$ to said first optical waveguide, and applying said coherent light beam with a bandwidth $\Delta f_2$ to said reference optical waveguide, wherein $$\Delta f_1 \cdot \Delta f_2 \geq \tfrac{1}{2},$$

in order to obtain a very high signal-to-noise ratio.

24. A method as defined in claim 23, wherein said light beam directing step includes the steps of:
filtering said coherent light beam in order to obtain the narrow bandwidth $\Delta f_1$ for application to said first optical waveguide; and
filtering said coherent light beam in order to obtain the wide bandwidth $\Delta f_2$ for application to said reference optical waveguide.

25. A method as defined in claim 24, wherein said predetermined delay varying step includes the step of delaying the light beam through a degree range of 0° to 360°.

26. A method as defined in claim 25, further comprising the step of delaying the light beam applied to the other of said first or reference optical waveguides by a second delay in order to have a desired phase shift between the light propagating in said first optical waveguide relative to the light propagating in said reference optical waveguide prior to exposure of the first coating of said first optical waveguide to chemical agents.

27. A method as defined in claim 26, wherein said exposing step includes the step of exposing said first optical waveguide to a gas sample possibly containing said predetermined chemical agents.

28. A method as defined in claim 26, wherein said exposing step includes the step of exposing said first optical waveguide to a liquid sample possibly containing said predetermined chemical agents.

29. A method as defined in claim 20, wherein said coherent light detecting step includes the step of applying said coherent light beam to said first optical waveguide with a narrow bandwidth $\Delta f_1$ and to said reference optical waveguide with a bandwidth $\Delta f_2$, wherein $$\Delta f_1 \cdot \Delta f_2 \gtrsim 1,$$

in order to obtain a very high signal-to-noise ratio.

30. A method as defined in claim 18 further comprising:
   scanning said particular frequency of said light beam in a sequential manner to new frequencies over a desired band of frequencies.

* * * * *